United States Patent [19]

Katz

[11] Patent Number: 5,166,219
[45] Date of Patent: * Nov. 24, 1992

[54] SYSTEMIC ANTI-INFLAMMATORY TREATMENT

[75] Inventor: David H. Katz, La Jolla, Calif.

[73] Assignee: Lidak Pharmaceuticals, La Jolla, Calif.

[ * ] Notice: The portion of the term of this patent subsequent to Dec. 3, 2008 has been disclaimed.

[21] Appl. No.: 737,492

[22] Filed: Jul. 29, 1991

Related U.S. Application Data

[63] Continuation-in-part of Ser. No. 430,822, Nov. 2, 1989, Pat. No. 5,070,107.

[51] Int. Cl.$^5$ .................. A01N 31/00; A01N 31/04; A61K 31/045; A61K 31/07

[52] U.S. Cl. .................................... 514/724; 514/725
[58] Field of Search .............................. 514/724, 725

[56] References Cited

U.S. PATENT DOCUMENTS 4,186,211  1/1980  Debat ................................ 514/724

Primary Examiner—Nathan M. Nutter
Attorney, Agent, or Firm—Grant L. Hubbard

[57] ABSTRACT

A method of arthritis and other inflammatory diseases in humans or other mammals, comprising introducing into the circulatory system of the human or other mammal to be treated a composition consisting essentially of at least one C-27 to C-32 aliphatic alcohol in a physiologically compatible carrier is disclosed.

16 Claims, 2 Drawing Sheets

SYSTEMIC ANTI-INFLAMMATORY TREATMENT

CROSS-REFERENCE TO RELATED APPLICATION

This is a continuation-in-part of the present inventor's co-pending patent application Ser. No. 430,822, Nov. 2, 1989 and now U.S. Pat. No. 4,070,107

1. Field of the Invention

This invention relates to alcohol-containing compositions that are useful in the systemic treatment of various inflammatory diseases and conditions as well as virus-induced diseases. More specifically, the present invention relates to a systemic anti-inflammatory disease treatment using a narrow class of aliphatic straight-chain saturated monohydric alcohols that have from 27 to 32.

2. Background of the Invention

It is well known that certain selected alcohols have some physiological activity. It is known, for example, that 1-triacontanol stimulates the growth of plants, see, e.g., Ries, Stanley K. and Sweeney, Charles C., U.S. Pat. No. 4,150,970. Interestingly, the C-30 alcohol triacontanol appears to possess this physiological activity, and the C-28 and C-32 do not possess such physiological activity, or at least have very much less physiological activity in plant growth, see, e.g., the patents and publications of Ries et al., ibid, and of Ashmead, Harvey H., Weleber, Andrew J., Laughlin, Robert G., Nickey, Donald O. & Parker, Dane. K, and Ohorogge, Alvin J.

Triacontanol has also been reported to accelerate the decomposition of sewage and reduce H2S, Starr, Jerry, U.S. Pat. No. 4,246,100.

Beeswax comprises, inter alia, esters of long-chain aliphatic alcohols having chain lengths in the area of interest, and it is known to obtain such alcohols by hydrolysis of beeswax. Beeswax has been used since antiquity in a great variety of cosmetic and therapeutic applications, as a base for lipstick, in lotions and creams, as an emollient and as a constituent in therapeutic products for topical and membrane application. Various constituents of beeswax and products derived from beeswax have also been used in cosmetic and therapeutic applications. For example, Slimak, Karen M., U.S. Pat. No. 4,793,991, describes a hypoallergenic cosmetic comprising single plant source beeswax. Gans, Eugen, Nacht, Sergio and Yeung, David have described the use of the non-polar saturated straight chain C-21 to C-33 hydrocarbon fraction of beeswax in the treatment of inflammatory skin disorders, U.S. Pat. No. 4,623,667.

The mechanisms of the rather diverse and unpredictable physiological effects of the various alcohols are, at best, poorly understood, and studies are not generally definitive. There appears to some interaction of certain n-alkanols with lipid bilayer membranes, Westerman, P. W., Pope, J. M., Phonphok, N., Dan, J. W., Dubro, D. W., Biochim Biophys Acta(NETHERLANDS) 939, 64–78 (1988), and studies have been conducted respecting the partitioning of long-chain alcohols into lipid bilayers, Franks N. P. & Lieb W. R., Proc Natl. Acad. Sci. USA 83 5116-20 (1986); cholesterol solubility of n-alkanols, Pal S. & Moulik S. P., Indian J Biochem Biophys 24-8 (1987); neurological effects of certain long-chain alcohols, Natarajan V. & Schmid H. H., Lipids 12 128-30 (1977); Snider S. R., Ann Neurol 16 723 (1984); Borg J., Toazara J., Hietter H., Henry M., Schmitt G., Luu B., FEBS Lett 213 406-10 (1987).

Levin, Ezra reported that tetracosanol, hexacosanol, octacosanol and triacontanol and their esters improved physical performance of athletes and disclosed compositions comprising such alcohols and esters in vegetable oil bases for oral ingestion, U.S. Pat. No. 3,031,376.

An incidental disclosure of a composition intended for topical application comprising a major portion liquified gaseous propellant and a minor portion of a mixture of C-12 to C-30 fatty alcohols that were used simply to mark the areas of application of the aerosol is contained in U.S. Pat. No. 3,584,115 to Gebhart.

Clark, U.S. Pat. No. 4,670,471 discloses the use of triacontanol, in a suitable carrier, as a treatment for inflammatory disorders such as herpes simplex, eczema, shingles, atopic dermatitis, psoriasis, etc. Clark performed experiments with the compositions of the type disclosed by Gebhart, U.S. Pat. No. 3,584,115 comprising an aerosol and a mixture of triacontanol and palmitic acid, which Clark indicates to be as effective as pure triacontanol, and concluded that the aerosol carrier destroyed the effect of triacontanol and that a hydrophilic carrier for triacontanol was necessary to achieve the desired anti-inflammatory effect. There is some reason to believe that Clark's composition was simply saponified beeswax that would contain triacontanol and palmitic acid, as Clark indicates, but which would also contain, as substantial constituents, hexacosanolic acid and various hydrocarbons. Gas chromatographic-mass spectrum analysis of various compositions believed to have been used by Clark were not definitive, but suggested that at least some such compositions were very complex mixtures, some of which may be lower alkanes, esters, acids or alcohols. Whether or not these were found by Cleark to be effective anti-inflammatory compositions is not known. McKeough, Mark & Spruance, S. L. evaluated the efficacy of 5% triacontanol in a branch chain ester base in the treatment of HSV-1 dorsal cutaneous infection in guinea pigs and concluded that the active ingredient in triacontanol is the long chain hydrocarbon (unpublished report in the file of U.S. Pat. No. 4,670,471).

Revici, Emanuel, Sherwood, Bob E., Benecke, Herman P., Rice, John M., and Geisler, Richard W., U.S. Pat. No. 4,513,008, disclose a method of inactivating enveloped virus using C-20 to C-24 polyunsaturated acids, aldehydes or alcohols having 5–7 double bonds, and referenced disclosures by Sands et al. Antimicrobial Agents and Chemotherapy 15, 67–73 (1979) (antiviral activity of C-14 to C-20 unsaturated alcohols having 1–4 double bonds), Snipes et al., Antimicrobial Agents and Chemotherapy 11, 98–104 (1977) (C-20 tetraenyl alcohol having low activity), and Symp. Pharm. Effects, Lipids (AOCS Monograph No. 5) 63–74 (1978) (suggesting lower antiviral activity for saturated long-chain alcohols).

Katz, Martin & Neiman, Herbert M, U.S. Pat. No. 3,592,930, disclose a medicant vehicle containing from 15 to 45 parts of saturated fatty alcohol from 16 to 24 carbons, along with glycol solvent, plasticizer, penetrant and adjuvant which is used as a carrier for antibiotics, steroids, antihistamines, etc. Ryde, Emma Marta & Ekstedt, Jan Erik, U.S. Pat. No. 3,863,633, disclose a composition for topical treatment of the eye that comprises a lipophilic substance, a hydrophilic swellable polymer and from 10 to 80% C-12 to C-22 surface active alcohols such as 1-docosanol, 1-hexadecanol, 1-octadecanol and 1-eicosanol that serve as a stabilizer for the mixture.

The content of the prior art and the corresponding skill in the art, relative to topically administered compositions, may be summarized as follows: short-chain alcohols, i.e. under about 16 carbons, tend to be irritants while longer chain alcohols, particularly the aliphatic alcohols tend to be non-irritating (Katz et al., supra). 1-Triacontanol, a 30-carbon unsaturated aliphatic alcohol, in a suitable hydrophilic carrier has (or, may have, depending upon the precise compositions used by Clark) value in treating inflammatory conditions of the skin (Clark, supra). Shorter chain C-10 to C-14 aliphatic alcohols demonstrate low level in vitro virucidal characteristics, while C-18 alcohols show no discernable virucidal activity in vitro (Snipes, supra). Polyunsaturated C-20 to C-24 alcohols inactive enveloped virus (Revici et al., supra). C-16 to C-24 aliphatic alcohols are useful as stabilizers in carrier compositions for drugs having diverse physiological activity.

Respecting aliphatic alcohols, one would predict from the studies of Snipes and Clark that, in the continuum of aliphatic alcohols from C-10 to C-30 virucidal activity, at a very low level, may appear (if in vitro studies may be used to predict in vivo results) in C-20 to C-14 alcohols (which would also be irritants as reported by Katz), that virucidal activity disappears in the C-16 to C-28 range and then appears uniquely (if Clark's compositions were pure triacontanol or mixtures of triacontanol with palmitic acid as he indicates) with the C-30 alcohol 1-triacontanol, which has been shown to have unique physiological effects in plant treatment.

Even considering the possible ambiguity of Clark's compositions, one would not predict any significant virucidal activity for aliphatic alcohols in the C-20 through C-28 chain length.

Notwithstanding the negative teachings of the prior art, the inventor has determined that these higher (C-27-C-32) aliphatic alcohols may be used, in suitable carrier compositions, in the systemic treatment of virus-induced disease and diseases induced by pathogenic organisms and has generally as an effective systemic anti-inflammatory disease treating composition.

SUMMARY OF THE INVENTION

The present invention is embodied in methods for preventing, inhibiting and treating infectious diseases generally, virus, bacterial, yeast and other microorganism-induced diseases and inflammatory diseases generally including antoimmune diseases, arthritis, etc. in humans or other mammals, comprising intravenous, intramuscular, transdermal or oral introduction into the human or other mammal to be treated of a composition consisting of one or more of C-27 to C-32 aliphatic alcohols in a physiologically compatible carrier, and to compositions suitable for carrying out such methods. The anti-inflammatory properties of n-docosanol or an immunologically-mediated disease process were tested to model certain human inflammatory diseases, such as autoimmune arthritis. Collagen-induced arthritis (CIA) is an autoimmune arthritic disease, Stuart, J. M., Townes, A. S., and Kang A. H., Ann. Rev. Immunol. 2:199–218, 1984, readily elicited in certain strains of rodents and sub-human primates by immunization with chick type II collagen emulsified in CFA. CIA exhibits many of the histologic features observed in patients with rheumatoid arthritis (RA), including infiltration and proliferation of mononuclear cells, synovial hyperplasia, pannus formation, and often severe osteolysis with destruction of joint cartilage and architecture. CIA pathology is dependent on cell-mediated immunity, Levin E., U.S. Pat. No. 4,031,376, and production of lymphokines such as IFN$\gamma$, Mauritz, N. J., Holmadahl, R., Jonsonn, R., Van der Meide, P. H., Scheynius, A., and Klareskog, L., Arth Rheum., 31:1297–1304, 1988. The development of CIA and RA is accompanied by the production of antibodies reactive with type II collagen, particularly those isotypes which can activate the complement cascade, Watson, W. C., and Townes, A. S., J. Exp Med. 162:1878–1891, 1985, Watson, W. C., Cremer, M. A., Wooley, P. H., and Townes, A. S., Arth. Rheum. 29:1316–1321, 1986. In the murine system, high levels of IgG2a anti-collagen antibody are associated with CIA susceptibility and course of disease. Similarly, patients with RA exhibit substantial levels of complement-fixing IgG3 anti-type II collagen antibodies. Passive transfer studies have demonstrated that the Ig fraction from serum of mice with CIA (containing high levels of IgG2a), or from serum of patients with RA (containing high levels of IgG3), can initiate a transient arthritis in normal murine recipients, Stuart, J. M., Townes, A. S., and Knag, A. H., Ann. Rev. Immunol. 2:199–218, 1984. The usefulness of CIA as a model for arthritis also stems from its dependence on inflammatory mediators and processes, Griswold, D. E., Hillegass, L. M., Meunier, P. C., DiMartino, M. J., and Hanna, N., Arth. Rheum. 31:1406–1412, 1988, a potential focus for the beneficial effects of n-docosanol.

DESCRIPTION OF THE PREFERRED EMBODIMENTS

Figure 1:
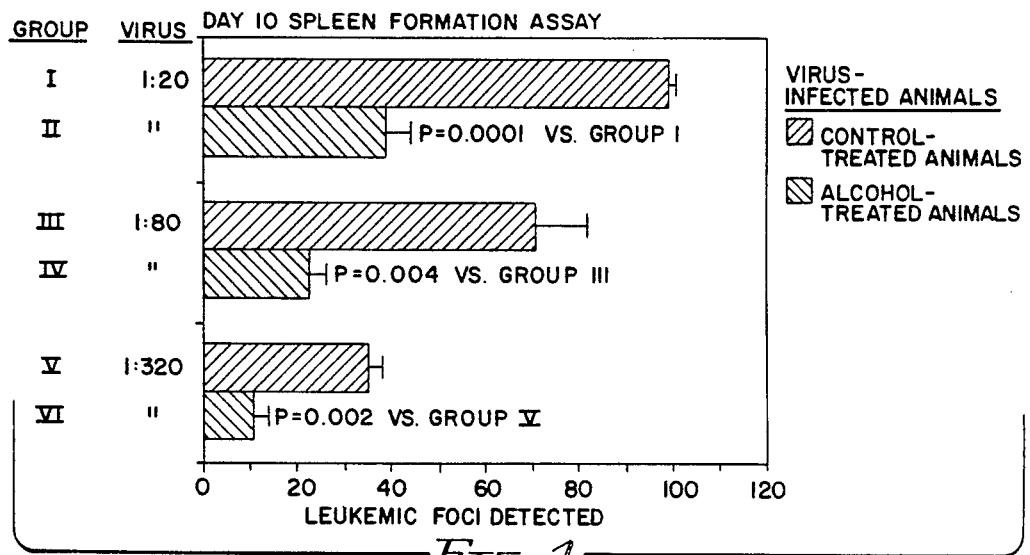
FIG. 1 depicts data showing the inhibition of Friend virus-induced erythroleukemia.

The method may be carried out using compositions in which the sole physiologically active agent(s) is the C-27 to C-32 aliphatic alcohol, or comparable compositions that may also include other physiologically active constituents that do not interfere with the efficacy of the C-27 to C-32 alcohols. Corresponding low molecular weight esters of these alcohols, e.g., methyl-, ethyl-, propyl-, etc., ester derivatives of these alcohols, and corresponding low-molecular-weight ester derivatives, e.g., formyl-, acetyl-, propyl-, etc., ester derivatives and other comparable derivatives of these alcohols are regarded as less preferred possible equivalents of the alcohols of this invention.

The composition of the carrier is not critical so long as the carrier is physiologically compatible with the blood and tissues of the human or other mammal to be treated and is substantially free from any interfering physiological effect.

Compositions suitable for intravenous or intramuscular injection into the human or mammal patient consist essentially of one or more aliphatic alcohols having from 27 to 32 carbons in the aliphatic chain of the alcohol(s) in a suitable carrier. For example, a suspension of from 0.1 mg/ml to 300 mg/ml of the indicated alcohol(s) suspended in a carrier solution of isotonic sodium chloride solution containing a suitable preservative, such as 0.1 to 1.5% benzyl alcohol, stabilizers such as from 0.25 to 1% carboxymethylcellulose sodium and 0.005 to 0.1% polysorbate 80, and sufficient sodium hydroxide or hydrochloric acid to adjust the Ph to 5.0 to 7.5, all percentages by weight, may be used for either intravenous or intramuscular injection.

Another composition suitable for intravenous or intramuscular injection into the human or mammal patient may consist essentially of one or more aliphatic alcohols having from 27 to 32 carbons in the aliphatic chain of the alcohol(s) in a suitable carrier in suspension of from 0.1 mg/ml to 300 mg./ml of such alcohol(s) suspended in a carrier solution of alcohol (1–10%), glycerin (10–20%) and water (balance 70–89%), along with suitable preservative.

Such compositions may be injected in suitable amounts to provide a dose to the patient of from 0.1 mg/50 kg body weight to 2 gm/50 kg body weight. It is desirable to achieve and maintain a level of the specified alcohol(s) in the body in the range of at least about 0.1 mg/kg of body weight.

The alcohol(s) to which this invention is directed may effectively be introduced through the mucus membrane system of the human or mammal patient. Such introduction may be, for example, through the vaginal, anal, oral or nasal membranes. The above liquid compositions which consist essentially of one or more aliphatic alcohols having from 27 to 32 carbons in the aliphatic chain of such alcohol(s) in a suitable liquid carrier may, for example, be used for trans-mucus membranal introduction of such alcohol(s) into the circulatory system of the human or mammal to be treated by, for example, introducing such liquid as an aerosol into the oral or nasal passages or as a liquid into the vaginal or anal passages of the body where these compounds reduce inflammation as well as act as anti-viral agents and pass through the membrane into the circulatory system of the patient where the compounds are effective systemic anti-inflammatory agents. In the latter applications, however, gels, creams or suppositories are more conveniently used.

In one convenient embodiment, the method of the invention comprises a composition consisting essentially of one or more aliphatic alcohols having from 27 to 32 carbons in the aliphatic chain of such alcohol(s) into the vagina, where it will inhibit the activity of the sperm and interfere with fusion of the sperm cell with the female egg cell. The alcohol composition of interest may, of course, be used in connection with a diaphragm or other contraceptive device if desired.

As indicated above, the alcohols of interest here will serve as contraceptive compositions. The mode of action has not been fully explored, but it is believed that these alcohols reduce the activity and viability of sperm and inhibit or prevent the sperm from attaching to and penetrating the egg, thus preventing fertilization.

Likewise, the alcohol-containing composition may be introduced through the anus as a local anti-inflammatory agent and from where it passes through the membrane into the circulatory system of the patient where it acts as a systemic anti-inflammatory agent. The specified alcohol(s) may be in any physiological acceptable form such as in cream or suppository compositions. An exemplary suppository may consist essentially of a composition consisting essentially of one or more aliphatic alcohols having from 27 to 32 carbons in the aliphatic chain of such alcohol(s) alone or in a concentration of from 0.05 mg alcohol(s)/gm of carrier to 400 (or higher) mg alcohol(s)/gm of carrier. Cocoa butter is a commonly used suppository carrier component, alone or in mixture with, for example, tartaric acid and malic acid. Polyethylene glycols of suitable molecular weight are also suitable suppository carriers. Suppositories may also include a preservative such as methylparaben or benzethonium chloride, and such acid or base components as are desired to adjust the pH to the range of about Ph 5 to Ph 7.5. Any of the above, or other, suitable suppository carrier compositions may be used with composition consisting essentially of one or more aliphatic alcohols having from 27 to 32 carbons in the aliphatic chain of such alcohol(s) to form a suitable contraceptive and/or anti-viral suppository. The suppository, to be commercially and aesthetically acceptable, must be a solid at ambient room temperature, i.e., generally in the range of about 27° C., and must melt at or slightly below normal body temperature, i.e., in the general range of about 37° C. These temperatures are, of course, only general ranges, and the precise melting point is not critical.

Trans-membranal introduction of such alcohol(s) may be accomplished by introducing small amounts of such alcohols neat, but such introduction is difficult to control and not efficient.

Cream and gel compositions consisting essentially of one or more aliphatic alcohols having from 27 to 32 carbons in the aliphatic chain of such alcohol(s) in concentrations of from about 0.1 mg/ml to 300 mg/ml (or higher) in a suitable cream or gel carrier may also be used effectively. Such a gel may, for example, comprise a suspension agent such as Carbomer ® polyacrylic acid cross-linked with allyl sucrose, polyethylene glycol, water and suitable preservatives. A suitable cream base may, for example, comprise white petrolatum, polyoxyethylene stearate, cetyl alcohol, stearyl alcohol, propylene glycol, isopropyl myristate, sorbitan monooleate and water along with suitable preservatives adjusted to a pH of from pH 5 to pH 7.5.

The alcohols of interest here may also be introduced for transmembranal passage into the human or mammal patient's circulatory system, as well as a prophylaxis against infection from airborne virus and other pathogenic microorganisms, through inhalation of a composition consisting essentially of one or more aliphatic alcohols having from 27 to 32 carbons in the aliphatic chain of such alcohol(s) in a suitable physiologically acceptable carrier. The liquid compositions mentioned before may, for example, be packaged in a nebulizer and introduced through nasal or oral passages in the customary manner. An exemplary composition consisting essentially of one or more aliphatic alcohols having from 27 to 32 carbons in the aliphatic chain of such alcohol(s) suspended in aerosol propellant such as trichloromonofluoromethane and/or dichlorodifluoromethane, along with diluents, preservatives, pH adjusting reagents, etc. The exemplary aerosol composition delivers essentially neat alcohol(s) to the mucus membrane. An exemplary ear drop composition delivers essentially neat alcohol(s) to the tympanic membrane. Comparable liquid drops may be applied using appropriate droppers to the eyes, ears and mouth for application to and passage through the membranes in these respective organs.

All trans-membranal compositions may, in addition to other ingredients, also include penetration enhancers.

A number of such enhancers are known as penetration enhancers and may be used in the compositions of this invention. One such vehicle is dimethyl sulfoxide, which is described in U.S. Pat. No. 3,551,554. Other such penetration enhancers are disclosed in U.S. Pat. No. 3,989,816; 3,991,203; 4,112,170; 4,316,893; 4,415,563; 4,423,040; 4,424,210; 4,444,762, sometimes referred to as Azone ®.

The anti-viral effectiveness of higher alcohols has been established in in nitro tests, as demonstrated in the following example.

EXAMPLE 1—Ecotropic Virus

A composition a composition consisting essentially of aliphatic alcohols having 22 carbons in the aliphatic chain in micelle suspension, 600 μg alcohol/ml PBS buffer, was introduced into cultures of LP-BM 5 MuLV ecotropic virus, 1000 PFU/ml, and the percent of virus inhibition, as compared with controls continuing only PBS buffer, indicated by cell-fusion activity and cell plaque count, using XC indicator cells (Virology 42:1136, 1970), was determined. The following table shows the viral inhibition as a function of concentration of the specified alcohols:

TABLE I

Percent LP-BM 5 Virus Inhibition as a function of C-22 Alcohol Concentration (μg/ml) ($10^2$ input)

| LP-BM 5 PFU/ml | 60 | 6 | 0.6 | 0.06 | 0 | (Control) |
|---|---|---|---|---|---|---|
| 100 | | 89 | 40 | 22 | 7 | 0 |

EXAMPLE 2—Ecotropic Virus

The effect of the C-20 to C-26 alcohols of this invention on ecotropic virus was further confirmed and compared with AZT.

TABLE II

| LP-BM 5 PFU/ml | Drug Concentration μg/ml | | | | |
|---|---|---|---|---|---|
| | 500 | 50 | 5 | 0.5 | medium |
| | Plaques/culture | | | | |
| $10^3$ Input | | | | | |
| C-22 Alcohol | 401 ± 5 | 562 ± 11 | 561 ± 50 | 703 ± 88 | 817 ± 14 |
| % decrease | 51 | 31 | 31 | 14 | 0 |
| AZT | 43 ± 6 | 131 ± 10 | 382 ± 59 | 657 ± 24 | 762 ± 43 |
| % decrease | 94 | 83 | 50 | 14 | 0 |
| Control (alcohol) | 733 ± 39 | 710 ± 72 | 700 ± 7 | 823 ± 14 | 702 ± 43 |
| % decrease | 0 | 0 | 0 | 0 | 0 |
| $10^2$ Input | | | | | |
| C-22 Alcohol | 13 ± 2 | 72 ± 24 | 84 ± 12 | 110 ± 2 | 131 ± 10 |
| % decrease | 90 | 45 | 36 | 19 | 0 |
| AZT | 5 ± 3 | 23 ± 5 | 43 ± 3 | 34 ± 3 | 108 ± 2 |
| % decrease | 95 | 79 | 60 | 69 | 0 |
| Control (alcohol) | 106 ± 6 | 106 ± 4 | 114 ± 7 | 99 ± 2 | 130 ± 11 |
| | 18 | 18 | 12 | 24 | 0 |

EXAMPLE 3

The effect of C-20 to C-26 alcohols on Friend virus-induced leukemia was investigated using the spleen focus formation assay (Virology 24:513, 1964). Balb/c mice were injected with 0.5 ml of the indicated dilution of virus. The mammals were then injected intravenously with 1 ml of either a control solution or a solution containing 0.5 mg C-20 to C-26 alcohols on days 0, 1 and 2 of the experiment. On day 10 of the experiment, the mammals were killed and their spleens placed into Bouin's fixative. The number of macroscopic leukemic cell foci in each of the spleens were then counted. The data are depicted in FIG. 1 as the geometric means and standard errors, with Groups I and II having 6 mammals each, and 5 mammals being in each of the remaining groups.

The discovery that these higher alcohols, including, by only modest extrapolation of the data, alcohols having a somewhat higher molecular weight, i.e., C-27 to C-32, which are naturally occurring and are essentially non-toxic in concentration ranges of interest have significant anti-viral effect is considered to be of major import inasmuch as the way is open to providing a safe and effective method for the treatment for virus diseases and for preventing or at least significantly reducing the likelihood of virus infection to the human or other mammal patient, without any significant side effects and without the need for as intense monitoring by the treating physician as is required with inherently toxic compounds.

As a treatment for acquired immunodeficiency syndrome (AIDS), as a method for prophylactic treatment of persons exposed to AIDS and/or carrying AIDS virus but without demonstrating AIDS symptoms, and as methods and compositions for preventing or reducing the risk of infection by AIDS and virus-induced diseases, as well as in the prevention and treatment of pathogenic microorganism-induced diseases generally, the present invention is regarded as a significant improvement.

Another important aspect of the invention is that it may provide a safe and effective mode of treatment of diseases resulting from infection of the patient with such lipid-containing virus as HTLV-1, HSV-1, HSV-2, cytomegalovirus (CMV), Epstein-Bar (EBV), and influenze viruses.

The risk of infection by such viruses as HIV, HSV-1, HSV-2, CMV, EBV, influenze viruses and other viruses which are communicated by personal contact, contact with contaminated blood or tissue or laboratory instruments or devices, aerosol transmission, etc., may be substantially reduced by the methods and compositions of the present invention.

It is believed that another mode of action of the alcohols of this invention is in the inhibition or prevention of malignant growth and/or metastasis. If, for example, cancer cells cannot metastasize, or the rate of metastasis is reduced, then the spread of cancer may be blocked or reduced. Significant inhibition of cancer cell metastasis coupled with natural or drug-induced death or destruction of existing cancerous cells will lead to partial or total remission of the disease. The same principal applies, of course, to any disease which is propagated by cell metastasis. Accordingly, the present invention is considered useful in the treatment of non-virus-induced diseases and diseases which are not dependent upon viral replication but which are spread by metastasis.

EXAMPLE 4

DBA/1 mice were injected intradermally at the base of the tail on days zero and 28 with 20 μg chick type II collagen emulsified in CFA. The mammals were followed for clinical signs of arthritis, i.e., joint erythema, edema, and loss of function. The data illustrated in FIG. 1 were derived from a series of 5 independently conducted experiments which show the clinical course of collagen-induced arthritis (CIA) in DBA/1 mice immunized with chick type II collagen/CFA. Male DBA/1 mice were immunized with 20 μg chick type Ii collagen emulsified in CFA on days zero and 28. The mammals were followed for a total of 70 days for clinical signs of arthritis, joint erythema, edema, and loss of function. That data represent the means and standard deviations of incidence of arthritis and spontaneous remission from 5 separate experiments using 10-15 mice per experiment. p As noted by others, Stuart, J. M., Townes, A. S., and Knag, A. H., Ann. Rev. Immunol. 2:199-218, 1984, collagen-immunized DBA/1 mice exhibit disease induction starting at about 20 days post-immunization, and peeking at about 50-60 days into the experiment. Histologic analysis (not shown) confirmed extensive mononuclear infiltration and pannus formation as reported by others using similar techniques, Wooley, P. H., Luthra, H. S., Stuart, J. M., and David, C. S., J. Exp. Med. 154:688-700, 1981. Arthritis was usually noted in the hind limbs, but a substantial fraction of the mammals exhibited disease in all four limbs. We used a four point scoring system where zero is a normal limb, 1 being marginal swelling and erythema, 2 being progressively more severe swelling, erythema, and lack of flexibility, and 3 being severe erythema, edema, and often complete fusion of the bone elements and lack of flexibility. The cumulative incidence of arthritis was on average 86% of the immunized mice, of which 92% exhibited a clinical score of 2-3 in at least one limb. Similar Immunization of BALB/c mice did not cause CIA, confirming the requirement for an appropriate genetic background to elicit this autoimmune disease, Wooley, P. H., Luthra, H. S., Stuart, J. M., and David, C. S., J. Exp. Med. 154:688-700, 1981.

Male DBA/1 (obtained from Jackson Laboratories, Bar Harbor, Me.) were used at 8 to 12 weeks of age. The mice were immunized intradermally at the base of the tail on day zero and again on day 28 with 20 μg chick type II collagen, prepared exactly as described by others, Trentham, D. E., Townes, A. S., and Kang, A. H., J. Exp. Med. 146:857-858, 1977, or obtained commercially (Genzyme, Boston, Ma.), emulsified in complete Freund's adjuvant (Difco, Ann Arbor, Mi.). The mammals were examined visually twice weekly for arthritic signs, swollen and erythremic limbs. Induction of CIA-associated histopathology was assessed by evaluation of paraffin sections of normal limbs, and limbs obtained from mammals with various stages of the disease essentially as described by others, Wooley, P. H., Luthra, H. S., Stuart, J. M., and David, C. S., J. Exp Med 154:688-700, 1981.

Figure 2:
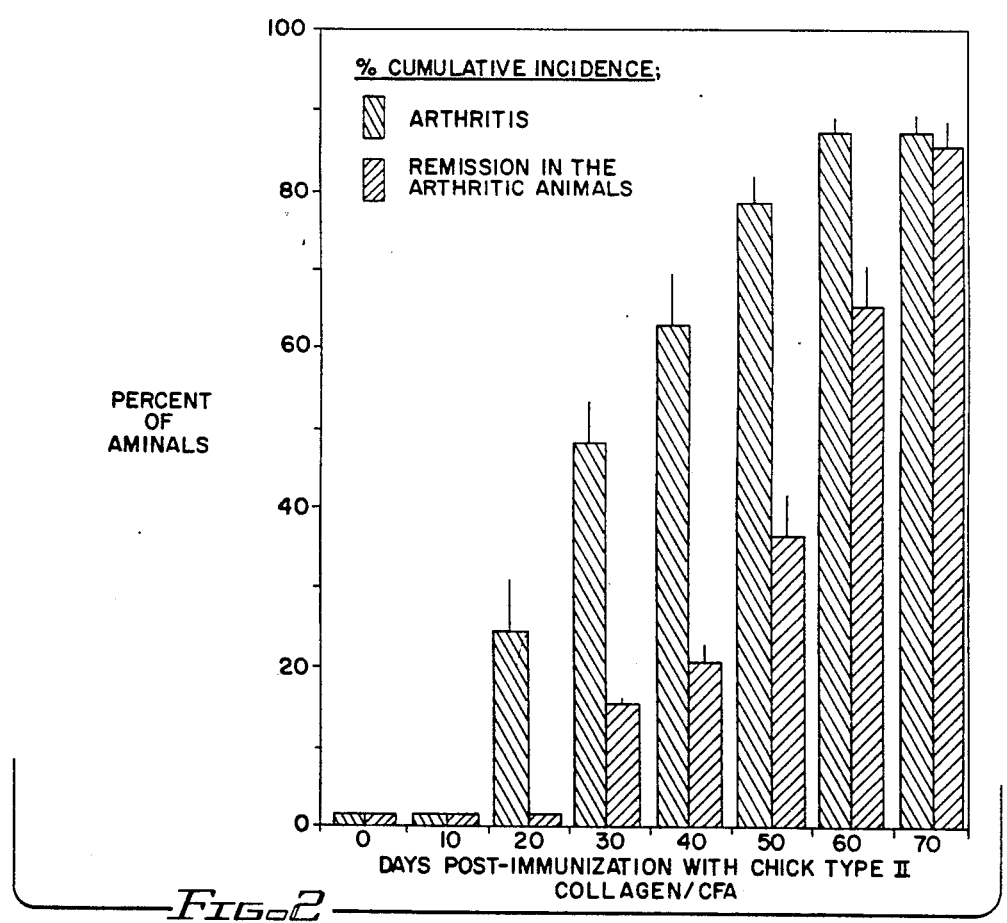
FIG. 2 depicts data showing the course of collagen-induced arthritis in DBA/1 mice immunized with chick type II collagen/cfa.

Spontaneous remission of CIA has been commonly observed in arthritic mice about 7-14 days after onset of the disease, Stuart, J. M., Townes, A. S., and Kang, A. H., Ann Rev. Immunol. 2:199-218, 1984. Thus, as seen in FIG. 2, the onset of remission and peak incidence follow that of arthritis by about 10 days each. Of those mammals which developed CIA, an average of 84% exhibited remission. Mammals in remission can redevelop arthritic signs, and again exhibit remission; CIA thus mimics RA in its cycling of exacerbation and remission of clinical signs.

EXAMPLE 5—Treatment OF CIA WITH N-DOCOSANOL n-Docosanol was suspended in Pluronic F68 ® (Trademark of BASF Corp; chemical composition, poloxamer 188, a non-ionic detergent block co-polymer of propylene oxide and ethylene oxide) as follows: Pluronic F-68 (mw 8,400; BASF Corp., Parsippany, N.J.) was diluted to 10 mg/ml in warm (37° C.) Dulbecco's high glucose modified Eagle's medium (DMEM; Whittaker Bioproducts, Walkersville, Md.), and the solution then heated to 50° C. n-Docosanol was added at 10 mg/ml to the Pluronic F-68 in DMEM and the solution further heated to 86° C. wile sonicating (Branson 450 sonifier) for 21 minutes at an initial output of 65 watts. The resulting stock suspension contained 10 mg/ml of n-docosanol particles of 0.03-0.3 microns. The corresponding control solution was prepared identically except the n-docosanol was excluded.

Figure 3:
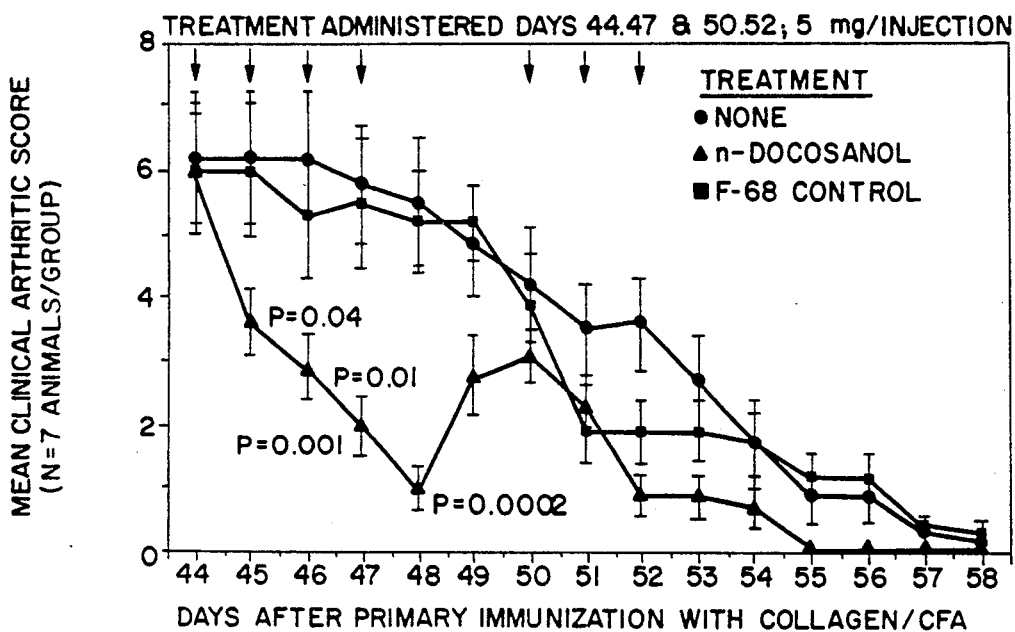
FIG. 3 depicts the effects of n-docosanol on collagen-induced arthritis in DBA/1 mice mean clinical arthritic score.
Figure 4:
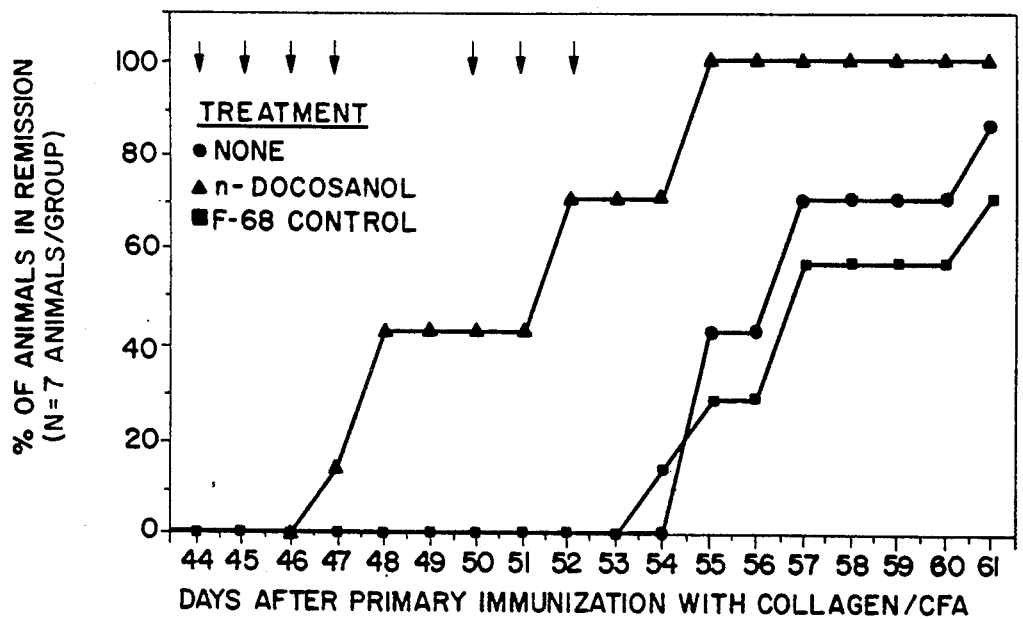
FIG. 4 depicts the effects of n-docosanol on collagen-induced arthritis in DBA/1 mice showing percent of animals in remission.

Adult DBA/1 mice were immunized with collagen/CFA as described in FIG. 3, and on day 44 after primary immunization the mammals were given a clinical score and placed in one of three groups. There were 7 mammals per group and each of the three groups exhibited a comparable man clinical score. One group was treated once daily with 5 mg of n-docosanol as indicated in FIG. 3 (0.5 ml of 10 mg/ml n-docosanol in 10 mg/ml Pluronic F-68), half of which was given intravenously and the other half given subcutaneously. Another group was treated with 5 mg Pluronic F-68 control in a similar manner. The last group was left untreated.

The effects of n-docosanol on CIA in DBA/1 Mice are depicted in FIG. 3. Adult DBA/1 male mice were immunized with collagen/CFA as described in the legend to FIG. 2. On day 44 after the primary immunization, arthritic mammals were placed in one of three groups with 7 mammals per group. One group was left untreated. One group was given 0.5 ml n-docosanol/Pluronic F-68, 0.25 ml of which was administered intravenously and the other half given subcutaneously. Such treatments were administered on days 44-47, and on days 50-52. The data are expressed as a mean arthritic score in panel A. A four point scoring system was used in which zero is a normal limb; 1 indicates marginal swelling and erythema, 2 indicates progressively more severe swelling, erythema, and lack of flexibility, and 3 indicates severe erythema, edema, and often complete fusion of the bone elements and lack of flexibility. In panel B, the data are expressed as a percent of arthritic mammals which exhibit complete clinical remission (panel B).

As shown in panel A of FIG. 3, each of the three groups of mammals exhibited a similar mean clinical score on day 44. The n-docosanol-treated group exhibited a significant decrease in mean clinical score 24 hours after the first treatment as contrasted to the untreated or the control-heated groups, which continued to decrease after each successive injection of n-docosanol. On day 49, or 48 hours after the last injection of n-docosanol, a rise in mean clinical score was observed in the n-docosanol-treated group. A further regimen of 3 n-docosanol treatments resulted in another significant decrease in mean clinical score as contrasted to the untreated ($P=0.001$) or the control-treated ($P=0.03$) groups. That the n-docosanol is the responsible active ingredient is attested to by the lack of consistent beneficial effect by the Pluronic F-68 control preparation.

As shown in panel B of FIG. 3, n-docosanol treatment hastened the occurrence of remission from CIA. Mammals exhibiting complete clinical remission could be observed as early as day 47 after primary immunization (3 days after the initial treatment) in the n-docosanol-treated group and 100% of that group were clinically normal by day 55. Remission in the untreated or the control-treated groups lagged that of the n-docosanol-treated group by 8–9 days, a pattern similar to that of untreated mammals illustrated in FIG. 2.

These data demonstrate the potential applicability of systemic administration of higher aliphatic alcohols in a suspension Pluronic F-68 formulation for the treatment of autoimmune arthritis. The rapidity with which n-Docosanol hastened remission of CIA suggests an anti-inflammatory, rather than immunosuppressive, effect. While this remains to be fully established, our previous findings regarding the inhibition of contact sensitivity by n-Docosanol cream would support this notion. The control F-68 solution failed to exhibit activity in the inhibition of CIA clinical signs documenting that n-docosanol is the active ingredient. This is the first demonstration of the potential therapeutic effects of n-docosanol for the systemic treatment of arthritis in general, and autoimmune arthritis in particular.

The methods of this invention are suitable for treating inflammatory diseases of any origin. Inflammation is reduced to permit the body to heal. In certain diseases the causative microorganism is also attacked directly, as established by the data present hereinbefore respecting virus. It has also been established that the methods of this invention are suitable for treating inflammatory diseases resulting from bacterial infections and infections by certain other microorganisms. The methods are considered suitable for treating parasitic diseases such as amebiasis, Chagas' disease, trypanosomiasis, leishmaniasis, malaria, pneumocystosis, toxoplasmosis, ancylostomiasis, ascariasis, clonorchiasis, cysticercosis, echinococcosis, fascioliasis, filariasis, paragonimiasis, strongyloidiasis, schistosomiasis, toxocariasis and trichinelliases and other infectious diseases such as pneumococcal pneumonia, streptococcal diseases, staphylococcal infections, Meningitis, and gonococcus infections, and certain yeast and fungal diseases.

It will be readily understood from the foregoing that the essential constituent(s) of the compositions useful in the present method is one or more aliphatic alcohols having from 27 to 32 carbons in the aliphatic chain of the alcohol(s), and that the composition of the carrier is non-critical and subject to great variation.

Industrial Application

This invention is useful in treating inflammatory diseases generally, including autoimmune and microorganism-induced inflammatory diseases of humans and other mammals.

What is claimed is:

1. A method of treating inflammatory disease in humans or other mammals, comprising introducing into the circulatory system of the human or other mammal in need of such treatment a physiologically effective amount of a composition consisting essentially of at least one C-27 to C-32 aliphatic alcohol in a physiologically compatible carrier.

2. The method of claim 1 wherein composition consists essentially of C-22 aliphatic alcohol in a physiologically compatible carrier comprising propylene oxide and ethylene oxide block co-polymer non-ionic detergent.

3. A method of treating inflammatory disease in humans or other mammals, comprising introducing into the circulatory system of the human or other mammal in need of such treatment by intramuscular injection a physiologically effective amount of a composition consisting essentially of at least one C-27 to C-32 aliphatic alcohol in a physiologically compatible carrier.

4. The method of claim 3 wherein composition consists essentially of C-22 aliphatic alcohol in a physiologically compatible carrier comprising propylene oxide and ethylene oxide block co-polymer non-ionic detergent.

5. A method of treating inflammatory disease in humans or other mammals, comprising introducing into the circulatory system of the human or other mammal in need of such treatment by trans-mucus membranal penetration a physiologically effective amount of a composition consisting essentially of at least one C-27 to C-32 aliphatic alcohol in a physiologically compatible carrier.

6. The method of claim 5 wherein composition consists essentially of C-22 aliphatic alcohol in a physiologically compatible carrier comprising propylene oxide and ethylene oxide block co-polymer non-ionic detergent.

7. A method of treating inflammatory disease in humans or other mammals, comprising introducing into the human or other mammal in need of such treatment by transdermal penetration a physiologically effective amount of a composition consisting essentially of at least one C-27 to C-32 aliphatic alcohol in a physiologically compatible carrier.

8. The method of claim 7 wherein composition consists essentially of C-22 aliphatic alcohol in a physiologically compatible carrier comprising propylene oxide and ethylene oxide block co-polymer non-ionic detergent.

9. A method of treating arthritis in humans or other mammals, comprising introducing into the circulatory system of the human or other mammal in need of such treatment a physiologically effective amount of a composition consisting essentially of at least one C-27 to C-32 aliphatic alcohol in a physiologically compatible carrier.

10. The method of claim 9 wherein composition consists essentially of C-22 aliphatic alcohol in a physiologically compatible carrier comprising propylene oxide and ethylene oxide block co-polymer non-ionic detergent.

11. A method of treating arthritis in humans or other mammals, comprising introducing into the circulatory system of the human or other mammal in need of such treatment by intramuscular injection a physiologically effective amount of a composition consisting essentially of at least one C-27 to C-32 aliphatic alcohol in a physiologically compatible carrier.

12. The method of claim 11 wherein composition consists essentially of C-22 aliphatic alcohol in a physiologically compatible carrier comprising propylene oxide and ethylene oxide block co-polymer non-ionic detergent.

13. A method of treating arthritis in humans or other mammals, comprising introducing into the circulatory system of the human or other mammal in need of such treatment by trans-mucus membrane penetration a physiologically effective amount of a composition consisting essentially of at least one C-27 to C-32 aliphatic alcohol in a physiologically compatible carrier.

14. The method of claim 13 wherein composition consists essentially of C-22 aliphatic alcohol in a physiologically compatible carrier comprising propylene oxide and ethylene oxide block co-polymer non-ionic detergent.

15. A method of treating arthritis in humans or other mammals, comprising introducing into the circulatory system of the human or other mammal in need of such treatment by transdermal penetration a physiologically effective amount of a composition consisting of at least one C-27 to C-32 aliphatic alcohol in a physiologically compatible carrier.

16. The method of claim 15 wherein composition consists essentially of C-22 aliphatic alcohol in a physiologically compatible carrier comprising propylene oxide and ethylene oxide block co-polymer non-ionic detergent.

* * * * *